United States Patent
Loustauneau et al.

(10) Patent No.: US 8,705,691 B2
(45) Date of Patent: Apr. 22, 2014

(54) DENTAL X-RAY APPARATUS AND ASSOCIATED METHOD

(71) Applicant: Trophy, Croissy Beaubourg (FR)

(72) Inventors: Vincent Loustauneau, Fontenay-Sous-Bois (FR); Sylvie Bothorel, Paris (FR); Colombe Isabelle Maury, Ozoir-la-Ferriere (FR)

(73) Assignee: Trophy, Croissy Beaubourg (FR)

( * ) Notice: Subject to any disclaimer, the term of this patent is extended or adjusted under 35 U.S.C. 154(b) by 0 days.

(21) Appl. No.: 13/751,392

(22) Filed: Jan. 28, 2013

(65) Prior Publication Data

US 2013/0208849 A1    Aug. 15, 2013

Related U.S. Application Data

(63) Continuation of application No. 12/745,775, filed as application No. PCT/FR2008/001680 on Dec. 3, 2008, now Pat. No. 8,363,780.

(30) Foreign Application Priority Data

Dec. 3, 2007  (FR) ...................................... 07 59516

(51) Int. Cl.
*A61B 6/14*    (2006.01)
*A61B 6/00*    (2006.01)

(52) U.S. Cl.
USPC ................................................. 378/38; 378/4

(58) Field of Classification Search
USPC .................................... 378/11, 13, 19, 38, 39
See application file for complete search history.

(56) References Cited

U.S. PATENT DOCUMENTS

| | | |
|---|---|---|
| 5,677,940 A | 10/1997 | Suzuki et al. |
| 6,118,842 A | 9/2000 | Arai et al. |
| 6,289,074 B1 | 9/2001 | Arai et al. |

(Continued)

FOREIGN PATENT DOCUMENTS

| | | |
|---|---|---|
| EP | 1609417 | 12/2005 |
| JP | 4280793 | 6/2009 |

(Continued)

OTHER PUBLICATIONS

Lee et al., "Development of a Digital Panoramic X-ray Imaging System for Dental Applications", 2007 IEEE Nuclear Science Symposium Conference Record, M13-193, pp. 2987-2990.

(Continued)

*Primary Examiner* — Irakli Kiknadze
(74) *Attorney, Agent, or Firm* — Young & Thompson

(57) ABSTRACT

A dental X-ray apparatus of the conical-beam digitized-tomography type includes: an X-ray generator emitting an X-ray beam towards an object and provided with a collimation element for collimating the emitted beam; an X-ray sensor having an active surface arranged opposite the generator; wherein the generator and the sensor can rotate simultaneously about a rotation axis, the sensor being oriented so that a longitudinal axis extending from the generator to the sensor through the rotation axis is perpendicular to the active surface of the sensor, the center of the sensor being transversally offset relative to the projection of the axis on the sensor's active surface, the arrangement of the collimation element and the sensor thus offset defining that the collimated beam illuminates the sensor's active surface while leaving a peripheral area of the surface that is faintly illuminated by the collimated beam relative to the rest of the active surface.

22 Claims, 4 Drawing Sheets

(56) References Cited

U.S. PATENT DOCUMENTS

| | | |
|---|---|---|
| 6,619,839 B2 | 9/2003 | Yoshimura |
| 6,944,259 B2 | 9/2005 | Yang |
| 7,099,428 B2 | 8/2006 | Clinthorne et al. |
| 7,236,563 B2 | 6/2007 | Sa et al. |
| 7,315,608 B2 | 1/2008 | Sa et al. |
| 7,424,091 B2 | 9/2008 | Park et al. |
| 7,486,759 B2 | 2/2009 | Suzuki et al. |
| 7,508,903 B2 | 3/2009 | Nishide et al. |
| 8,290,119 B2 | 10/2012 | Tancredi et al. |
| 2001/0036246 A1 | 11/2001 | Graumann |
| 2004/0190678 A1 | 9/2004 | Rotondo et al. |
| 2004/0258195 A1 | 12/2004 | Hara |
| 2005/0063507 A1 | 3/2005 | Baba et al. |
| 2007/0081624 A1 | 4/2007 | Nabatame |
| 2009/0041191 A1 | 2/2009 | Suzuki et al. |

FOREIGN PATENT DOCUMENTS

| | | |
|---|---|---|
| JP | 4313376 | 8/2009 |
| WO | 2004075118 | 9/2004 |
| WO | 2006013325 | 2/2006 |
| WO | 2008028988 | 3/2008 |
| WO | 2008092009 | 7/2008 |

OTHER PUBLICATIONS

D11, i-CAT's Operator's Manual, Cone Beam volumetric Tomography and Panoramic Dental Imaging System, 990400, Aug. 24, 2007.

D6, Soredex 30 years re. IDS2007.

D7, Customer re. IDS2007.

D8, Close fig. of customer re. IDS2007.

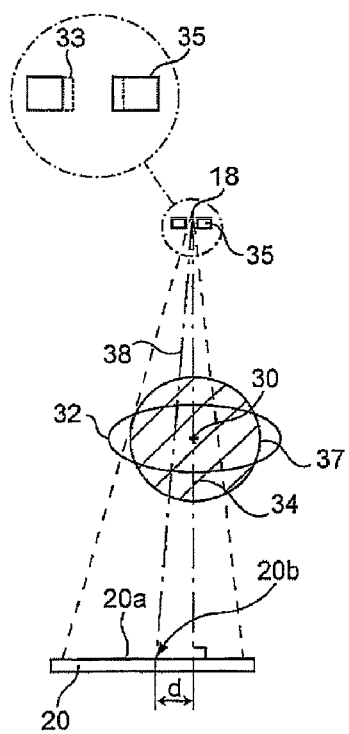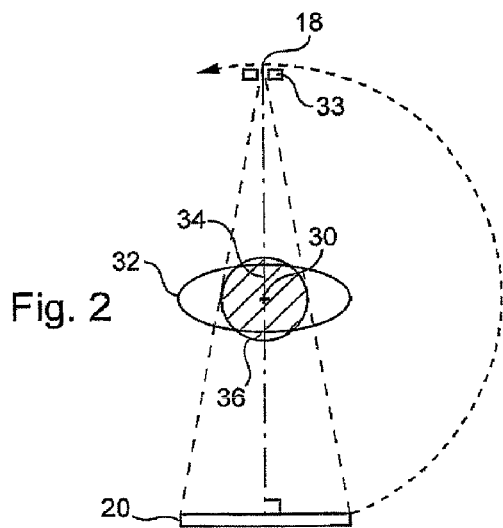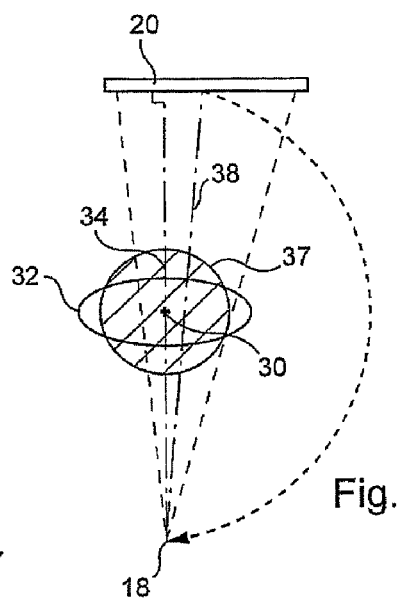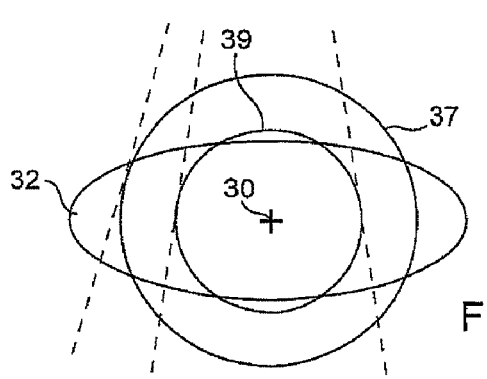
Fig. 2
Fig. 3a
Fig. 3b
Fig. 3e

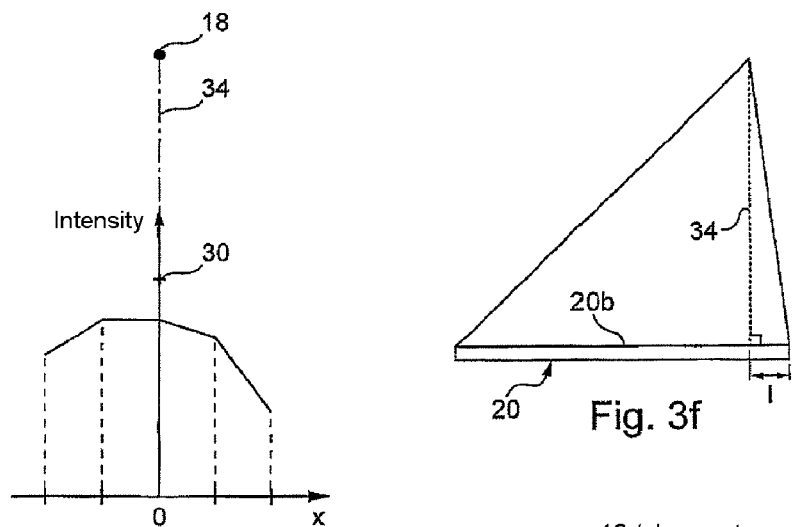
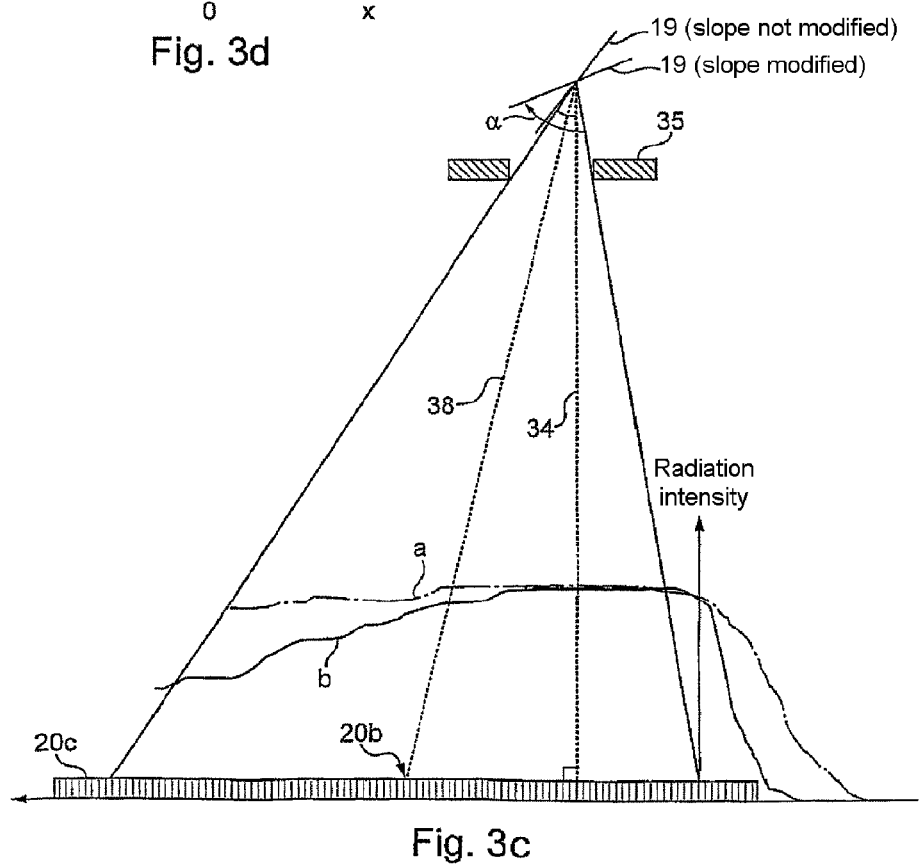

DENTAL X-RAY APPARATUS AND ASSOCIATED METHOD

The invention concerns dental X-ray apparatus and an associated method.

BACKGROUND OF THE INVENTION

In the field of dental radiology known X-ray apparatus comprises an X-ray generator and an X-ray sensor each mounted on one arm of an arch-shaped structure.

DESCRIPTION OF THE RELATED ART

To X-ray the jaw of a patient, the latter is installed in a seated position under the arch and their head is placed between the X-ray generator and the sensor close to the head. The X-rays are emitted by the source in the form of a cone directed toward the head. The sensor receives the rays that have irradiated the head of the patient, converts them into electrical signals, and supplies at the output an irradiated head image signal.

The arch pivots 360° about a vertical rotation axis so as to be able to obtain a plurality of image signals of the head of the patient at different angles.

For example, one image signal or shot can be obtained for each degree of rotation of the arch.

Until now, to examine in three dimensions an object such as a dental half-arch, the arch carrying the sensor and the generator is rotated 360° around the object.

To increase the width of the radiographically reconstructed volume, the width of the sensor must be increased accordingly.

Increasing the size of the sensor is reflected in a high additional cost.

For example, the volume that it is possible to reconstitute in the plane of the object from a plane sensor with dimensions of 5 cm×6 cm is approximately 3.2 cm×4 cm. The dimensions of the reconstituted volume take into account the conical geometry of the beam of X-rays and the respective distances between the point of emission of the rays (the focus of the source or the point on the anode on which the electron beam is focused), the object and the sensor.

A volume reconstructed in this way is insufficient to reconstitute an image size corresponding to a dental half-arch.

SUMMARY OF THE INVENTION

It would consequently be beneficial to be able to increase the size of the image reconstructed from a sensor with given dimensions.

The present invention therefore provides dental X-ray apparatus of the cone beam computed tomography type, comprising:
 an X-ray generator adapted to emit a beam of X-rays toward an object and provided with collimation means adapted to collimate the emitted beam,
 an X-ray sensor having an active surface disposed facing the generator, the generator and the sensor being adapted to be moved simultaneously in rotation about a rotation axis, characterized in that the sensor is oriented in such a manner that a longitudinal axis extending from the generator to the sensor and passing through the rotation axis is perpendicular to the active surface of the sensor, the center of the sensor being offset transversely relative to the projection of the axis onto the active surface of the sensor, and the arrangement of the collimation means and the sensor offset in this way being such that the collimated beam illuminates the active surface of said sensor leaving a peripheral area of said surface weakly illuminated by the collimated beam compared to the rest of the active surface.

The sensor offset must be significant to increase the volume of the reconstructed object but without being too high in order not to acquire image portions of no utility (unrelated to the object of interest) and not to mask areas of interest of the object.

Accordingly, in each angular position of the sensor and the generator, the latter cooperate to acquire an image of a laterally offset part of the object whereas in the prior art the captured image was centered on the object.

Thanks to this arrangement, on moving around the object a greater lateral extent (perpendicular to the longitudinal axis that joins the sensor and the generator and passes through the rotation axis thereof) of the object is captured by the generator plus sensor system.

This therefore makes it possible to reconstitute a larger object volume than before using the same sensor.

It will furthermore be noted that the X-ray generator illuminates only the part of the object situated in alignment with the offset sensor in a given angular position.

As the generator plus sensor system turns, the cone of X-rays emitted by the generator sweeps different areas or parts of the object during successive rotations, instead of always sweeping the central area of the object.

Accordingly, a given area of the object receives a lower dose of X-rays than the central area swept by the cone of X-rays in the prior art.

It will nevertheless be noted that the diaphragm or collimator of the X-ray generator is also offset in a corresponding fashion so that the emitted beam of X-rays illuminates the area of interest of the object over at least part of the surface of the offset sensor. The collimated beam is thus itself also offset in order to be centered on the sensor, for example.

Thus the central axis of the beam links the generator to the center of the sensor and is therefore also offset relative to the longitudinal axis perpendicularly connecting the generator to the sensor and passing through the rotation axis.

Furthermore, radiation diffused by the object is used more efficiently than in the prior art.

Moreover, the beam is collimated in such a fashion that a peripheral area of the active surface of the offset sensor is relatively weakly illuminated by this beam compared to the central part of the active surface that constitutes the greater part of that surface.

This weakly illuminated area or fringe makes it possible to ensure that the maximum intensity of the beam of X-rays illuminates the greater part of the active surface of the sensor and the intensity of the beam is considerably reduced beyond this, i.e. in the peripheral area. The unilluminated peripheral area therefore provides an X-ray safety function (radioprotection).

In practice, the mean intensity of the radiation received in the peripheral area is between 25% and 35% inclusive of the mean intensity of the radiation received in the remaining part of the sensor to provide an effective radioprotection function.

It will be noted that the beam collimated in this way is obtained by adjusting the collimation means, which can take the form of one or more collimation slits, for example.

The minimum width of the peripheral area is the width that makes it possible to obtain at the edge of the sensor a radiation intensity that is sufficiently low relative to the maximum intensity received by the central part of the active surface.

According to one feature, the sensor and the generator are adapted to be rotated in a rotation plane through which the rotation axis passes.

According to one feature, the center of the sensor is positioned transversely relative to the projection of the longitudinal axis on the active surface of the sensor at a distance which, measured in the rotation plane, is at most equal to the difference between the half-width of the sensor and a width sufficient to leave the peripheral area of the active surface of the sensor weakly illuminated compared to the rest of the active surface, the width of the sensor being the dimension measured perpendicularly to the longitudinal axis in the rotation plane.

This maximum offset produces the maximum effectiveness linked to the offset, notably in terms of reconstruction volume and irradiated area.

According to one feature, the center of the sensor is offset by a distance between one quarter of the width of the sensor and the aforementioned maximum distance that is slightly less than the half-width of the sensor, allowing for the relatively weakly illuminated peripheral area.

The width of the peripheral area is appropriate to provide this safety function taking account of the accuracy of installing and positioning the various elements: sensor, collimation and generator means, beam accuracy.

This width thus represents, for example, a plurality of pixels between the illuminated active surface part of the sensor and its edge.

According to one feature, the arrangement of the collimation means and the sensor is such that the collimated beam illuminating the active surface of the sensor is delimited by an edge that is placed as close as possible to the projection of the axis onto the active surface at a minimum distance that makes it possible to obtain a minimum overlap area during rotation of the generator and the sensor.

This ensures a minimum overlap volume with the object to be illuminated during rotation of the generator and the sensor in order to be able to reconstruct a three-dimensional representation of the object that is free of artifacts.

In practice, the minimum distance considered is of the order of two pixels of the matrix of pixels forming the active surface of the sensor.

This distance is generally less than the width of the unilluminated peripheral area of the sensor.

According to one feature, the anode slope of the generator is modified as a function of the offset position of the sensor in order to render more uniform the profile of the radiation illuminating the active surface of the sensor offset in this way. This new configuration of the anode slope completes the new geometry obtained with the sensor offset and the collimation means adjusted as described above.

According to one particular feature, the angle between the anode slope of the generator and the longitudinal axis is open in the direction toward which the sensor is offset.

The intensity of the radiation produced by the generator and illuminating the offset sensor is thus increased and the profile of the radiation that reaches the sensor is rendered more homogeneous.

In practice, the value of the aforementioned angle increases.

According to one feature, the rotation plane is horizontal.

According to one feature, the rotation axis is vertical.

The invention also provides a method of reconstitution of a three-dimensional representation of an object irradiated by X-rays from plane dental radiographic images, said method employing an X-ray generator and an X-ray sensor that are adapted to be moved simultaneously in rotation about a rotation axis, the method comprising the following steps:

emission of a beam of X-rays toward an object from the X-ray generator and collimation of this beam by collimation means, reception by the sensor of the collimated beam of X-rays having irradiated the object, characterized in that the beam of X-rays is collimated onto the active surface of the sensor the center of which is offset transversely relative to the projection on the active surface of the sensor of a longitudinal axis extending from the generator to the sensor and passing through the rotation axis, a peripheral area of the active surface of the sensor offset in this way being weakly illuminated by the collimated beam compared to the rest of the active surface.

By plane radiographic image is meant a radiographic image of the object in three dimensions projected onto a plane.

This method has the same advantages as the apparatus briefly described above and they will therefore not be repeated here.

According to one feature, the sensor and the generator are adapted to be moved in rotation in a rotation plane through which the rotation axis passes.

According to one feature, the center of the sensor is positioned transversely relative to the projection of the longitudinal axis onto the active surface of the sensor at a distance which, measured in the rotation plane, is at most equal to the difference between the half-width of the sensor and a width sufficient to leave the peripheral area of the active surface of the sensor weakly illuminated compared to the rest of the active surface, the width of the sensor being the dimension measured in the rotation plane perpendicularly to the longitudinal axis.

According to one feature, the center of the sensor is positioned at a distance between one quarter of the width of the sensor and the maximum distance inclusive.

According to one feature, the arrangement of the collimation means and the sensor is such that the collimated beam illuminating the active surface of the sensor is delimited by an edge that is placed as close as possible to the projection of the axis onto the active surface at a minimum distance that makes it possible to obtain a minimum overlap area during rotation of the generator and the sensor.

According to one feature, the anode slope of the generator is modified as a function of the offset position of the sensor in order to render more uniform the profile of the radiation illuminating the active surface of the sensor offset in this way.

According to one feature, the angle between the anode slope of the generator and the longitudinal axis is open in the direction toward which the sensor is offset.

According to one feature, the method includes a step of simultaneous movement of the sensor and the generator in rotation about the rotation axis in a plurality of successive angular positions and the method includes for each of these successive angular positions a step of the sensor providing a signal representative of a plane radiographic image of the irradiated object in that angular position, all the signals provided by the sensor for all the successive angular positions containing all the data necessary for the reconstruction of a representation in three dimensions of the object.

According to one feature, the movement of the sensor and the generator is effected over one rotation, which makes it possible to obtain sufficient data to reconstitute the whole of the object or an area of interest thereof in three dimensions.

According to one feature, the method includes a step of processing the signals supplied by the sensor for all successive angular positions in order to reconstruct the representation of the object in three dimensions.

According to one feature, the processing includes a filtering step for differentiating noise associated with the signals from the useful information present in the signals.

According to one feature, the filtering includes a step of independent decomposition of the various frequency bands present in the signals.

According to one feature, the processing includes a pyramidal type decomposition multiple scale filtering step.

According to one feature, the processing includes a step of weighting the data from the various signals and coming from parts of the object successively illuminated by the beam of X-rays during the successive rotations, the weighting being adjusted as a function of the presence or non-presence of the illuminated parts of the object in an area of the latter called the overlap area that is always illuminated by the beam during successive rotations.

Thus different weighting coefficients are assigned to the data according to its position relative to the areas successively swept by the cone of X-rays.

This weighting takes into account the lateral offset of the sensor described above.

BRIEF DESCRIPTION OF THE DRAWING FIGURES

Other features and advantages will become apparent in the course of the following description, given by way of nonlimiting example only and with reference to the appended drawings, in which:

FIG. 2 is a diagrammatic plan view showing the arrangement of the sensor and the generator in the prior art;

FIGS. 3a and 3b are diagrammatic plan views showing the arrangement of the sensor and the generator of the invention in two angular positions;

FIG. 3c shows the modification of the anode slope for an eccentric configuration of the sensor;

FIG. 3d is a diagrammatic view showing the intensity of the beam of X-rays as a function of its inclination relative to the longitudinal axis 34;

FIG. 3e is a diagrammatic partial view to a larger scale of FIG. 3a showing the overlap area;

FIG. 3f represents diagrammatically the offset position of the sensor for obtaining a minimum overlap area.

DETAILED DESCRIPTION OF THE INVENTION

Figure 1:
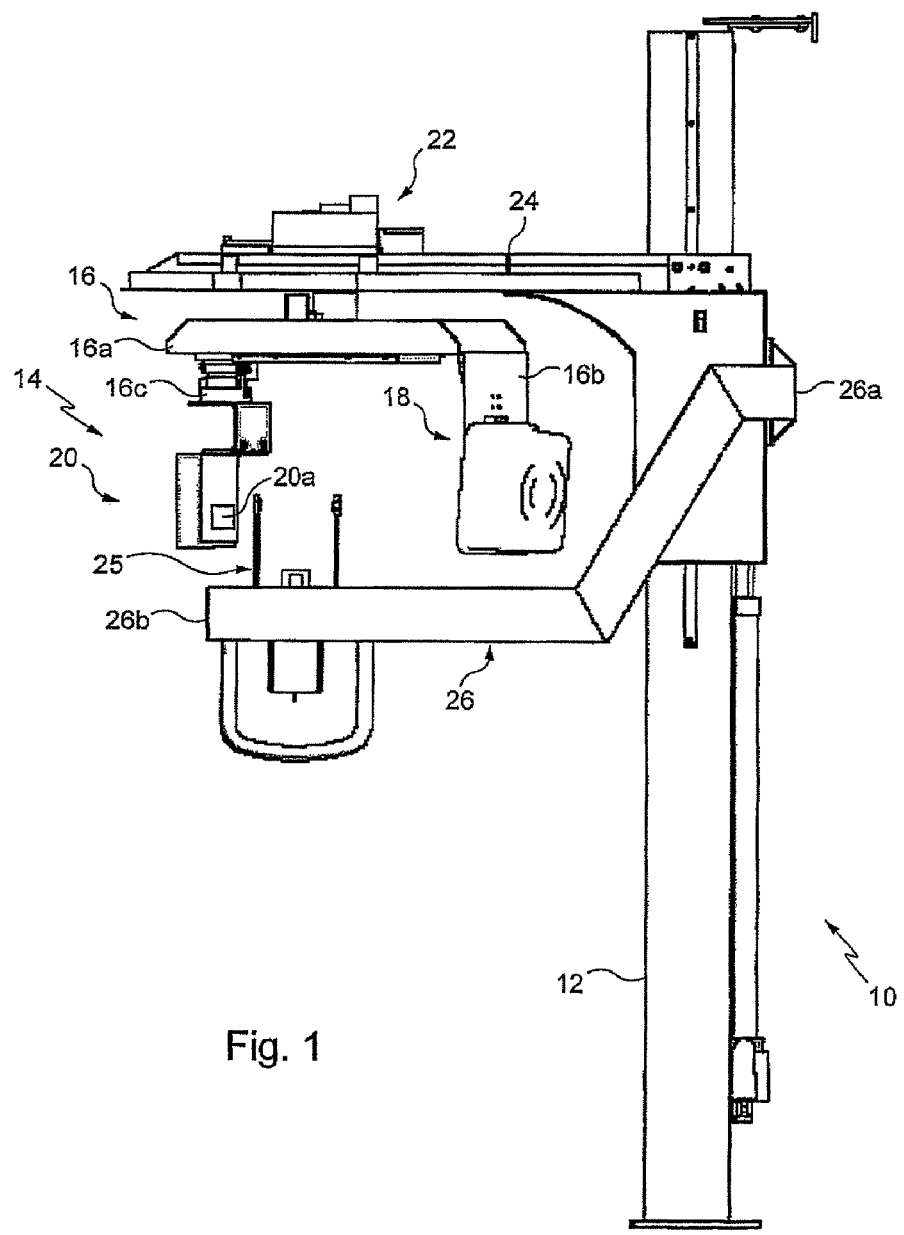
FIG. 1 is a diagrammatic general perspective view of dental X-ray apparatus of the invention.

As shown in FIG. 1, the dental X-ray apparatus 1 of the invention is of the CBCT (Cone Beam Computed Tomography) type. This apparatus makes it possible to acquire three-dimensional images of an object. The apparatus includes a fixed frame 12, for example a vertical beam, on which is mounted a rotatable X-ray unit 14 described next.

This unit includes an arch-shaped (C-shaped) mobile structure 16 including a central horizontal beam 16a that constitutes the body of the C and two vertical arms 16b and 16c extending downward from the horizontal beam and that constitute the two branches of the C.

An X-ray source or generator 18 is fixedly mounted on the arm 16b and an X-ray sensor 20 is mounted on the arm 16c.

The generator 18 and the sensor 20 are thus disposed facing each other and are in a fixed geometrical relationship relative to each other.

The structure 16 that serves as a support for the generator 18 and the sensor 20 constituting the core of the rotatable X-ray unit 14 is connected to a table 22 that is disposed above the structure 16 and is mobile in directions X and Y.

More particularly, this table is mounted on a horizontal beam 24 fixed to the vertical frame 12.

This table is able to be moved in the directions X and Y in a horizontal plane, thus making it possible to effect a complete rotation (360°) about a vertical rotation axis not represented in this figure.

This table makes it possible to position the center of rotation (the axis of rotation) of the structure on an object to be radiographed, notably an area of interest of the patient, without the latter needing to be moved.

It will be noted that the structure 16 connected to the table 22 is thus able to rotate about a vertical rotation axis positioned relative to the patient.

During this rotation, the generator 18 and the sensor 20 do not move relative to each other.

It will be noted that the table 22 also makes it possible to effect programmable panoramic trajectories when the apparatus is used in that application.

The X-ray apparatus 10 also includes a lower arm 26 fixed by one end 26a to the frame 12. The free end 26b of the arm is equipped with a positioning device 25 making it possible to immobilize the head of the patient during the taking of radiographic images when the apparatus is in operation. The head is therefore placed between the generator 18 and the sensor 20.

The X-ray generator 18 more particularly includes an X-ray tube, for example of the fixed anode type, the size of the focus of which is equal to 0.5 mm, for example.

This generator further includes collimation means for collimating a beam of X-rays generated by the generator 18. Those means include for example a collimation window or slit (diaphragm) that is sealed and dimensioned to produce a conical beam of X-rays intended to illuminate part of the head of the patient (for example the jaw) and the sensor disposed behind.

It will be noted that the width of the slit is adjustable to adjust the width of the beam and can equally be oriented differently in order to orient the beam in a given direction. The slit may be offset laterally, for example.

In a variant that is not represented, the collimation means may include a plurality of slits of diverse shape and/or size that can be switched in front of the generator and make it possible to adjust the width of the beam and/or its shape and/or its geometrical orientation to suit the offset position of the sensor.

The sensor 20 is attached to a motorized arm 16c that makes it possible to pivot the equipment carried by this arm about a vertical axis and, according to the chosen application, to position in front of the generator either the sensor 20 intended for three-dimensional examination of the object to be irradiated or a strip cassette (not shown) intended for a panoramic examination.

It will be noted that the sensor 20 used to reconstitute in three dimensions an object (e.g. the head of the patient) is a plane sensor.

This sensor is able, on the one hand, to receive X-rays coming from the generator 18 and having illuminated the object placed between the sensor and the generator and, on the other hand, to transform that radiation into an electrical signal representative of a radiographic image of the object.

The sensor more particularly includes, for example:
a converter that is able to convert X-rays received by the sensor into visible radiation; this converter is a cesium iodide scintillator, for example, and
a detector of the converted visible radiation coming from the converter that provides at the output of the sensor the electrical signal representative of a radiographic image of the object.

A plate of optical fibers doped with metal particles to absorb X-rays that are not converted is placed between the scintillator and the detector, for example.

This plate is for example the XR5 plate sold by the company Hammamatsu or the 47A plate from the company Schott.

It will be noted that the detector is for example a CMOS detector, which is preferable to a CCD type detector for effecting cone beam computer tomography. In fact, the Applicant has realized that such a component is more appropriate if it is required to reduce the dose of radiation given the large number of projections obtained during a 360° rotation of the sensor plus generator system. The use of an active matrix CMOS detector is advantageous.

More particularly, a biCMOS technology active pixel matrix with a high pixel fill factor can advantageously be used. The pixel matrix has a pixel size of the order of 120 microns, for example, and makes it possible to read captured images quickly, for example in 15 milliseconds.

Reducing the size of the detector relative to the size of the object to be reconstructed ensures that it is possible to fabricate the detector in the CMOS technology given the size of the wafers available. Such CMOS detectors have a high signal to noise ratio.

The size of the plane sensor is for example 5 cm×6 cm.

Alternatively, when it is required to reconstruct a voluminous object, a TFT type sensor can advantageously be used, for example.

A scintillating layer, for example in gadolinium oxysulfide or cesium iodide, is deposited on the detector to convert X-rays into visible radiation.

The optically active surface 20a of the sensor 20 is represented in FIG. 1.

FIG. 2 illustrates the conventional arrangement of a source of X-rays and the associated X-ray sensor relative to the position of the object to be irradiated placed between them.

Thus it is seen that the rotation axis of the sensor 20 and the generator 18, indicated in FIG. 2 by the dot 30 and positioned relative to the object 32 to be illuminated, is placed on the alignment axis 34 (longitudinal axis) that connects the generator 18 perpendicularly to the sensor 20.

This axis 34 constitutes the axis of the collimated beam of X-rays shown diagrammatically in this figure, emitted by the generator 18 and impinging on the center of the sensor 20 after having encountered the vertical axis 30.

The beam of X-rays is collimated by a slit 33 centered on the central axis 34 of the beam.

Note that in this prior art configuration, during the rotation movement of the generator and the sensor about the object 32 to be illuminated the beam of X-rays emitted by the generator always sweeps the same central area 36 of the object 32.

The lateral areas of the object 32 on either side of the central area 36 are not illuminated and thus the information that they contain is not captured by the beam of X-rays.

It will be noted that the generator 18 and the sensor 20 both move in a rotation plane that is perpendicular to the vertical rotation axis 30 and is the plane of FIG. 2.

FIGS. 3a and 3b illustrate the positioning of the sensor plus generator system of radiology apparatus of the invention in two different angular positions 180° apart.

In FIG. 3a, which is a view in a horizontal plane analogous to that of FIG. 2, the sensor 20 is laterally offset in this plane relative to its position in FIG. 2 (achieved by movement in translation of the sensor). The collimation slit 35 of the X-ray generator 18 is also laterally offset in a corresponding fashion so that the collimated beam illuminates most of the active surface of the offset sensor and is centered thereon. The offset slit 35 is shown in the part of FIG. 3a to a larger scale where the position of the slit 33 from FIG. 2 is also shown, in dashed line.

With the sensor and the generator laterally offset in this way, the central axis 38 of the cone of X-rays collimated by the slit of the generator 18 that impinges on the center of the sensor 20, which may be considered the alignment axis of the sensor and the generator, is no longer concurrent with the vertical rotation axis 30 as in FIG. 2 but rather alongside it (FIG. 3a).

It will be noted that the sensor 20 is oriented so that the longitudinal axis 34 that connects the generator perpendicularly to the active surface 20a of the sensor 20 passes through the rotation axis 30. The width of the sensor is the dimension of the sensor measured perpendicularly to the axis 34 in the FIG. 3a rotation plane.

The offset of the sensor can thus be defined as the transverse offset d of the center of the sensor 20b relative to the projection of the longitudinal axis 34 onto the active surface 20a.

As represented in FIGS. 3a and 3b, a small part 20c of the active surface of the sensor is separated by the beam, the edges of which are shown in dashed line, from the central part where the center 20b of the sensor is placed and that receives the maximum radiation intensity. The part 20c that forms a peripheral area around the central part with dimensions smaller than those of the remaining part of the sensor receives radiation of low average intensity relative to the medium intensity radiation that is received by the central part and is between 25% and 35% inclusive of that average intensity, for example.

For example, the width is equal to 10 pixels.

The geometry of this area is obtained by adjusting the width between the spaced edges of the slit 35 or alternatively by selecting a collimation slit of appropriate width from a plurality of slits.

The dental radiology apparatus provided in this way with an offset sensor and collimation means adjusted to produce a collimated beam projecting onto the active surface of the sensor the image of the collimation means (e.g. the image of the edges of the slot 35) makes it possible to optimize the reconstruction in three dimensions of the object (jaw or jaw portion) at the same time as providing an X-ray protection function.

In the case of 3D examination, the generator can advantageously be oriented to increase the intensity of the beam emitted and to improve the homogeneity of the illumination produced by the beam.

This orientation is effected by increasing the angle α between the anode slope 19 and the axis 34 (FIG. 3c).

In the configuration with the sensor offset by the maximum distance, the angle α is increased from 5° (anode slope not modified) to 7°.

It will be noted that, generally speaking, the new value of the angle α depends on the sensor offset. More particularly, this new value corresponds to the arctangent of the ratio of the offset distance to the distance between the focus of the generator and the surface of the sensor.

As shown in FIG. 3c, the increase in the angle α makes it possible to extend the irradiated surface and to render uniform the radiation profile on the active surface of the offset sensor. The optimized profile is represented by the curve a and the curve b shows the non-uniform radiation profile obtained with an unmodified anode slope. It will be noted that the intensity of the radiation illuminating the peripheral area bordering the sensor is much lower than the intensity in the complementary part of the sensor.

FIG. 3d shows the intensity of the beam of X-rays generated by the source 18 in the plane of the active surface of the sensor 20 as a function of the inclination of this beam (axis X) to the longitudinal axis 34. This intensity is measured in the plane of the sensor (not shown in this figure) and is at a maximum to the left of the axis 34, i.e. for an angular orientation of the beam at a non-zero angle to the axis 34. It is thus found that by orienting the anode slope of the generator as described above and as shown in FIG. 3c the maximum intensity of the beam tracks the sensor offset.

The value of the offset d of the sensor is limited by the necessity for an overlap area between all the areas or parts of the object 32 swept by the beam of X-rays during successive rotations of the sensor and the generator. This overlap area 39 (see FIG. 3e, which is enlarged view of part of FIG. 3a) corresponds in the rotation plane of the figure to a circle centered on the reference 30. However, it should be noted that the overlap area is three-dimensional and is a circular cylinder with revolution axis 30.

To illustrate the foregoing description, FIG. 3f represents a beam of X-rays illuminating the sensor in an offset position.

For simplicity, the object to be X-rayed and the peripheral X-ray protection area are not shown.

In this offset configuration, the maximum offset that it is possible to obtain corresponds to the half-width of the sensor less a width 1 that represents the minimum distance for which it is possible to obtain a sufficiently large minimum overlap area to be clear of artifacts during reconstruction of the object in three dimensions.

This width is the minimum distance between the projection of the axis 34 onto the surface of the sensor and the closest edge of the beam on the side opposite to that toward which the sensor has been offset.

In practice, this width is at least two pixels.

Thus the center 20b of the sensor is offset transversely from the projection of the longitudinal axis onto the active surface 20a of the sensor by a distance that is less than the half-width of the sensor (L/2) and is at most equal to L/2−1 for the reasons linked to the minimum overlap explained above.

Given the presence of the peripheral area 20c of the active surface of the sensor, when it is required to increase as much as possible the irradiated area for a given size of sensor the sensor can be offset at most by the distance L/2−1 less the width of this area 20c. This ensures a minimum overlap area.

From a practical point of view, the sensor is for example offset by a distance between one quarter the width of the sensor and the aforementioned maximum distance less than half that width inclusive.

For the aforementioned 5 cm wide sensor the lateral offset d is 2 cm, for example.

An offset less than one quarter of the width of the sensor (e.g. ⅛) can nevertheless be envisaged.

FIG. 3b represents the arrangement of the sensor and the generator after effecting a half-turn around the object 32 to be irradiated and it is seen that the area swept by the cone of X-rays emitted by the generator is not identical to the swept area in FIG. 3a.

It will be noted that these two areas overlap around the axis 30 and that they are combined into a swept volume with greater dimensions than those of the prior art area 36 shown in FIG. 2.

The volume that it is possible to reconstruct with the arrangement of FIGS. 3a-e is represented by the area 37 in the plane of those figures. This area 37 is of course three-dimensional and takes the form of a circular cylinder with revolution axis 30.

The invention thus makes it possible to cover more of the object to be irradiated for the same size of sensor and thus to increase the volume of data that it is possible to reconstruct radiographically in three dimensions.

When the invention is applied to the dental field, it therefore makes it possible to reconstitute in three dimensions an area of the jaw of a patient such as a dental half-arch with a sensor of small size compared to the prior art.

For example, a 2 cm lateral offset of a sensor with dimensions of 5 cm×6 cm makes it possible to reconstruct an object volume having dimensions of 5.8 cm×4 cm when projected onto a plane. In the absence of an offset, the dimensions when projected onto a plane of the volume that it is possible to reconstruct would be only 3.2 cm×4 cm.

It will be noted that the dimensions of the reconstituted volume take into account the geometry of the beam of X-rays and the respective distances between the point of emission of the rays, the object and the sensor.

The acquisition and the processing of the data by the rotary radiographic unit from FIG. 1 and from FIGS. 3a and 3b during one revolution of the assembly formed by the generator 18 and the sensor 20 in the new configuration described hereinabove and shown in FIGS. 3a to 3f and notably in FIG. 3c will now be described.

Thus an object to be X-rayed such as the head of a patient is placed between the generator 18 and the sensor 20 of FIG. 1 and the assembly formed by the generator and the sensor adopts a plurality of successive angular positions obtained by successive rotations of this assembly about the vertical rotation axis 30. The collimated beam of X-rays emitted by the generator illuminates in each position a different area of the object to be illuminated. This radiation is modified by its encounter with the object and the sensor placed in alignment with the generator receives the modified radiation.

Thus for each angular position in the rotation plane of the assembly formed of the generator and the sensor, the latter assembly receives radiation carrying information characteristic of the areas of the object illuminated by this radiation and transforms the received radiation into a signal representative of a plane radiographic image of the illuminated object in the angular position concerned (a 3D radiographic image of the object projected onto a plane).

The signal provided by the sensor in this way is referred to as a projection.

In the example described, the whole of the device formed by the generator and the sensor rotates one degree on each movement (step) of the rotary support structure, for example, and in this example a projection is obtained for each degree rotation.

It will be noted that with the sensor offset in accordance with the invention a complete rotation is necessary to acquire a sufficient quantity of data for reconstruction of the object in three dimensions.

These projections or signals are transferred to a data processing unit as and when they are obtained (or once only).

This data processing unit can be far away from the radiology apparatus 10, at a distance of the order of several meters or more.

The data processing unit is a computer such as a personal computer (PC), for example, storing one or more data files containing an algorithm for reconstruction of the object or an area of interest thereof in three dimensions.

The processing operations of the reconstruction algorithm applied to the data from the sensor takes account of the sensor offset.

Figure 4:
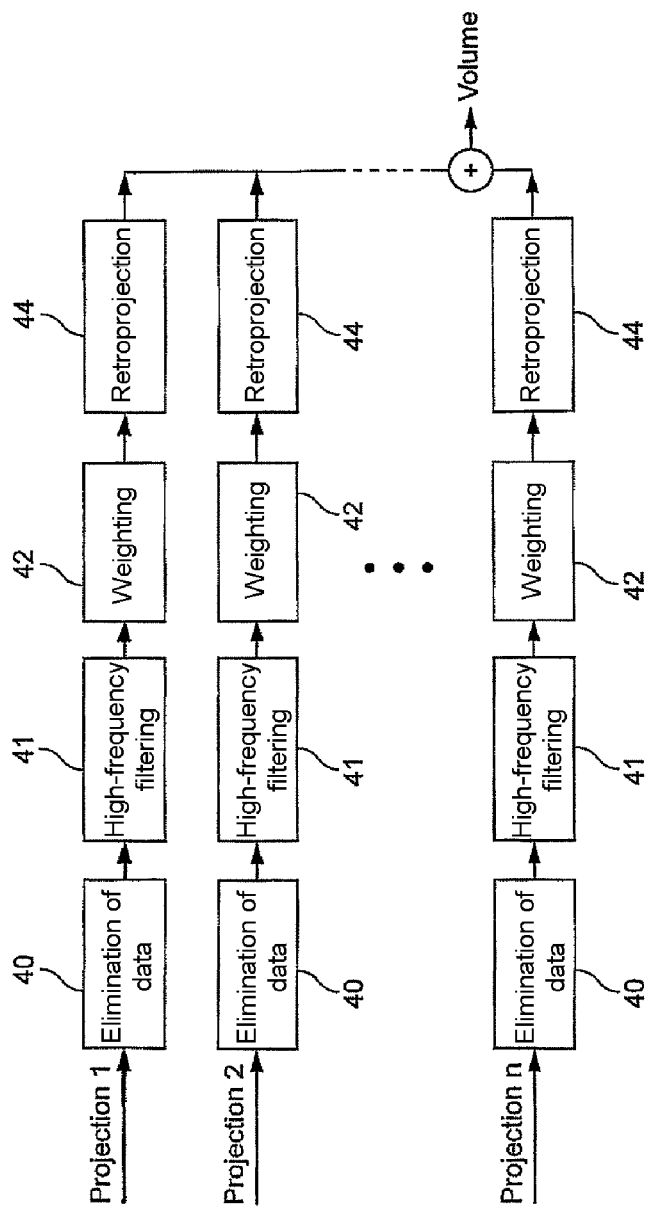
FIG. 4 is a diagram showing the operations of processing data provided by the sensor.

FIG. 4 is a diagram showing processing operations of an FDK algorithm or Feldkamp algorithm type reconstruction algorithm applied to each of the projections delivered by the sensor.

This algorithm, known in itself, has been modified in order to adapt to the aforementioned offset.

To be able to reconstruct the volume of the object (for example, the dental half-arch or tooth) the sensor offset in accordance with the invention must effect a rotation of 360° when a rotation of 180° suffices with a non-offset sensor of twice the width. Because of this, for a given angular step, fewer views are available with the offset sensor and the reconstruction noise is therefore higher.

In order to limit the effects of this noise, the algorithm illustrated in FIG. 4 advantageously comprises a first processing block 40 which removes from each projection 1 to n obtained successively during successive rotations of the sensor and the generator the data collected by the peripheral area 20c of the sensor and that does not concern the object because it surrounds only the latter. The position of this area is known as soon as the apparatus is placed in the new configuration and from then on it is easy to eliminate the corresponding data by calculation. It will be noted that reducing the volume of data to be processed by the algorithm to the subsequent blocks reduces the calculation volume and thus the calculation time.

The algorithm then includes a second processing block 41 that effects particularly high-frequency filtering of the data supplied by the sensor on each of the projections 1 to n after elimination of the data from the area 20c.

Generally speaking, the filtering effected by the block 41 makes it possible to distinguish noise associated with the signals collected by the sensor from useful information present in those signals by decomposing the various frequency bands that are found in the signals independently. In fact, the offset geometry has introduced reconstruction noise.

Each signal or projection is therefore filtered by the block 41 in which it undergoes pyramid type decomposition multiple scale filtering into frequency bands. It is more particularly a question of Gaussian difference type decomposition filtering. The algorithm that is used in this block 41 is iterative and provides for each frequency band of the signal concerned ramp type high-frequency pyramidal filtering.

The operation effected in this block consists more particularly in a plurality of successive steps during which:
- the image (projection) is undersampled by a power of 2 in the horizontal direction and by a factor 1 in the vertical direction,
- a mono-dimensional Gaussian difference is applied to each sample previously obtained,
- the result of the preceding step is combined in a weighted manner with the high-frequency image from the lower stage previously oversampled by two. The weighting laws are adjusted so as to discriminate the noise from the useful information.

The steps are repeated as many times as the size of the image (projection) is able to contain powers of 2.

The result of all the filtering applied to the signal, from the lowest frequency to the highest frequency, is thus obtained on exit from the block 41.

This step makes it possible to identify easily in the data noise components and the frequencies of interest in each signal.

This discrimination between noise and useful frequencies is furthermore effected in a short calculation time because of the iterative process.

The FIG. 4 algorithm advantageously includes a third processing block 42 applied to the data coming from the block 41 and intended to homogenize the overlap area with the non-overlap areas of the X-rayed object.

Generally speaking, each signal or projection filtered in the block 41 is multiplied in the block 42 by a weighting function that takes account of the redundancies that exist between the data coming from the various signals or projections, given the overlap area 39 (part or area of the object illuminated continuously by the beam of X-rays as it rotates).

Generally speaking, the weighting is adjusted as a function of the location relative to the overlap area 39 (FIG. 3e) of the parts of the object illuminated by the beam of X-rays during the successive rotations of the sensor and the generator and which have successively given rise to the various signals supplied by the sensor.

The weighting function applied in the block 42 is continuous and regular. More particularly, this function varies between 100% and 0% of the edge of the image corresponding to the pixels of the sensor 20 at the greatest distance from the longitudinal axis 34 at the edge of the image corresponding to the pixels of the sensor closest to that axis.

In particular, the value of the weighting function is ½ on the rotation axis 30, for example.

Weighted in this way, the filtered projections are processed by the next block 44 which retroprojects these projections.

This known retroprojection step of the conventional FDK algorithm retroprojects each filtered and weighted projection in order to reconstitute each voxel (elementary unit of volume that is directly linked to the size of the pixel in the plane of the object or the area of interest) of the X-rayed object or an area of interest thereof.

More particularly, during this step, all the voxels situated on the path of the X-rays concerned are assigned a value that depends on the value of the pixel reached by those rays in the projection concerned.

These four operations of the respective blocks 40, 41, 42, 44 are repeated for each projection by adding the result of the retroprojection operation obtained for a given projection to the volume already reconstructed from the preceding retroprojections.

It is then possible to reconstruct the object or an area of interest thereof in slices. A representation in three dimensions of the object or an area of interest thereof can therefore be reconstituted from an X-ray sensor of small size compared to the size of the sensor that would have been necessary in the absence of offsetting.

The invention claimed is:

1. A dental cone beam computed tomography X-ray apparatus, comprising:
   an X-ray sensor having an active surface including a first area and a second area; and
   an X-ray generator simultaneously movable with the sensor in rotation about a rotation axis to emit an X-ray beam toward the sensor, the generator having a collimator collimating the emitting X-ray beam and illuminating the first and second areas of the sensor, the collimated X-ray beam illuminating the first area of the active surface with an intensity greater than the illumination of the second area so as to provide the second area with a X-ray safety function, the sensor oriented such that a longitudinal axis extending from the generator to the sensor and passing through the rotation axis is perpendicular to the active surface of the sensor, a center of the sensor being offset transversely relative to a projection of the axis onto the active surface of the sensor.

2. The apparatus according to claim 1, wherein the sensor and the generator are rotatable about a rotation plane through which the rotation axis passes.

3. The apparatus according to claim 2, wherein the center of the sensor is positioned transversely relative to the projection of the longitudinal axis on the active surface of the sensor at a distance which, measured in the rotation plane, is at most equal to the difference between the half-width of the sensor and a width sufficient to leave the second area of the active surface of the sensor weakly illuminated compared to the rest of the active surface, the width of the sensor being the dimension measured perpendicularly to the longitudinal axis in the rotation plane.

4. The apparatus according to claim 3, wherein the center of the sensor is positioned at a distance between one quarter of the width of the sensor and the maximum distance inclusive.

5. The apparatus according to claim 2, wherein the rotation plane is horizontal.

6. The apparatus according to claim 1, wherein the arrangement of the collimator and the sensor is such that the collimated beam illuminating the active surface of the sensor is delimited by an edge that is placed as close as possible to the projection of the axis onto the active surface at a minimum distance that makes it possible to obtain a minimum overlap area during rotation of the generator and the sensor.

7. The apparatus according to claim 1, wherein an anode slope of the generator is modified as a function of the offset position of the sensor in order to render more uniform the profile of radiation illuminating the active surface of the sensor offset in this way.

8. The apparatus according to claim 7, wherein an angle α between the anode slope of the generator and the longitudinal axis is open in the direction toward which the sensor is offset.

9. The apparatus according to claim 1, wherein the rotation axis is vertical.

10. A method of reconstitution of a 3D X-ray image of an object, the method including:
  providing an X-ray generator and an X-ray sensor simultaneously movable in rotation about a rotation axis, the sensor having an active surface including a first area and a second area, the sensor oriented such that a longitudinal axis extending from the generator to the sensor and passing through the rotation axis is perpendicular to the active surface of the sensor, a center of the sensor is offset transversely relative to a projection of the axis onto the active surface of the sensor;
  emitting a beam of X-rays from the generator toward the object;
  collimating the emitted X-ray beam using a collimator toward the first and second areas of the active surface of the sensor; and
  illuminating the first area of the active surface with an intensity greater than the illumination of the second area so as to provide the second area with a X-ray safety function.

11. The method according to claim 10, wherein the sensor and the generator are adapted to be moved in rotation in a rotation plane through which the rotation axis passes.

12. The method according to claim 11, wherein the center of the sensor is positioned transversely relative to the projection of the longitudinal axis onto the active surface of the sensor at a distance which, measured in the rotation plane, is at most equal to the difference between the half-width of the sensor and a width sufficient to leave the second area of the active surface of the sensor weakly illuminated compared to the rest of the active surface, the width of the sensor being the dimension measured in the rotation plane perpendicularly to the longitudinal axis.

13. The method according to claim 12, characterized in that the center of the sensor is positioned at a distance between one quarter of the width of the sensor and the maximum distance inclusive.

14. The method according to claim 10, wherein the arrangement of the collimator and the sensor is such that the collimated beam illuminating the active surface of the sensor is delimited by an edge that is placed as close as possible to the projection of the axis onto the active surface at a minimum distance that makes it possible to obtain a minimum overlap area during rotation of the generator and the sensor.

15. The method according to claim 10, characterized in that an anode slope of the generator is modified as a function of the offset position of the sensor in order to render more uniform the profile of the radiation illuminating the active surface of the sensor offset in this way.

16. The method according to claim 15, wherein an angle α between the anode slope of the generator and the longitudinal axis is open in the direction toward which the sensor is offset.

17. The method according to claim 15, wherein processing includes a step of weighting the data from the various signals and coming from parts of the object successively illuminated by the beam of X-rays during the successive rotations, the weighting being adjusted as a function of the presence or non-presence of the illuminated parts of the object in an area of the latter called the overlap area that is always illuminated by the beam during successive rotations.

18. The method according to claim 10, further comprising simultaneous moving the sensor and the generator in rotation about the rotation axis in a plurality of successive angular positions, wherein each of the successive angular positions of the sensor provides a signal representative of a plane radiographic image of the irradiated object in that angular position, all the signals provided by the sensor for all the successive angular positions containing all the data necessary for the reconstruction of the object.

19. The method according to claim 18, further comprising processing the signals supplied by the sensor for all successive angular positions to reconstruct the object in three dimensions.

20. The method according to claim 19, further comprising filtering for differentiating noise associated with the signals from the useful information present in the signals.

21. The method according to claim 20, wherein filtering includes a step of independent decomposition of the various frequency bands present in the signals.

22. The method according to claim 20, wherein processing includes a pyramidal type decomposition multiple scale filtering step.

* * * * *